US007639362B2

(12) United States Patent
Ye et al.

(10) Patent No.: US 7,639,362 B2
(45) Date of Patent: Dec. 29, 2009

(54) PHOTONIC CRYSTAL SENSOR (75) Inventors: Jing Yong Ye, Ann Arbor, MI (US); Yunbo Guo, Ann Arbor, MI (US); Theodore B. Norris, Dexter, MI (US); James R. Baker, Jr., Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 322 days.

(21) Appl. No.: 11/881,040

(22) Filed: Jul. 25, 2007

(65) Prior Publication Data
US 2008/0225293 A1 Sep. 18, 2008

Related U.S. Application Data (60) Provisional application No. 60/833,101, filed on Jul. 25, 2006.

(51) Int. Cl.
*G01N 21/55* (2006.01)

(52) U.S. Cl. .................................................. 356/445
(58) Field of Classification Search .................. 356/445
See application file for complete search history.

(56) References Cited

U.S. PATENT DOCUMENTS 6,956,651 B2 * 10/2005 Lackritz et al. ............. 356/445
2007/0229835 A1 * 10/2007 Smolyaninov et al. ...... 356/445
2008/0062418 A1 * 3/2008 Magnusson et al. ......... 356/307

* cited by examiner

*Primary Examiner*—Roy Punnoose
(74) *Attorney, Agent, or Firm*—Harness, Dickey & Pierce, P.L.C.

(57) ABSTRACT

A photonic crystal sensor for outputting an output signal using a light source. The photonic crystal sensor includes a photonic crystal structure and a defect member disposed adjacent the photonic crystal structure. The defect member defines an operative surface. An input light signal from the light source is inputted to the photonic crystal structure and defect member and is internally reflected to thereby output the output signal. Also, the output signal relates to a condition at the operative surface.

22 Claims, 8 Drawing Sheets

| SYSTEM | DETECTION RANGE | RESONANCE WIDTH | EXPERIMENTAL SENSITIVITY | DETECTION LIMIT | TEMPERATURE STABILITY |
|---|---|---|---|---|---|
| PC-TIR | $10^{-5}$ nm ~ 700 nm | $\Delta\lambda = 8$ nm $\Delta\theta = 0.4°$ | 0.002 nm | $1.5 \times 10^{-5}$ nm | -0.012 nm/K |
| SPR | $10^{-3}$ nm ~ 200 nm | $\Delta\lambda = 40$ nm $\Delta\theta = 2°$ | 0.01 nm | $3 \times 10^{-3}$ nm | -0.25 nm/K |

PHOTONIC CRYSTAL SENSOR

CROSS-REFERENCE TO RELATED APPLICATIONS

This application claims the benefit of U.S. Provisional Application No. 60/833,101, filed on Jul. 25, 2006, the disclosure of which is incorporated herein by reference.

GOVERNMENT RIGHTS

This invention was made with government support under RR021893 awarded by the National Institutes of Health. The government has certain rights in the invention.

FIELD

The present disclosure relates to a photonic crystal and, more particularly, relates to a photonic crystal sensor.

BACKGROUND

The statements in this section merely provide background information related to the present disclosure and may not constitute prior art.

Photonic crystals (PC) are periodic dielectric structures with a band gap forbidding propagation of a certain frequency range of light. It is understood that controlling photon modes by PC structures can be useful. For example, electromagnetic waves can be bent with high efficiency around 90-degree corners within radii smaller than a wavelength with two-dimensional (2D) PC structures. Furthermore, a 3D PC can be used to control the timing of light emitted by a quantum dot. Moreover, a dual core photonic crystal fiber can be used for enhancing two-photon fluorescence biosensing sensitivity.

Selection from various types of PCs depends on specific applications. For example, 3D PCs are used in order to control spontaneous emission. In the case of controlling laser beams which are close to plane waves, a 1D PC is sufficient and preferable due to its simplicity in fabrication. Additionally, 1D PCs are used in various applications, such as an omnidirectional reflector, low-threshold optical switching, and non-linear optical diodes.

Furthermore, a technique has been developed for enhancing fluorescence by sandwiching the sample of interest (e.g., chromophores) between two pieces of 1D PCs. When a structural defect is introduced in the PCs, a photon-localized state can be created in the photonic band gap and the electric field around the defect member is enhanced. In one embodiment, two-photon fluorescence emission from 2-aminopurine in the PC structure was enhanced by a factor of 120. However, the application of this approach is limited because the thick substrate of the PC structure inhibits the sample from being observed with an optical microscope or from interacting with other biomolecules.

SUMMARY

A photonic crystal sensor is disclosed for outputting an output signal using a light source. The photonic crystal sensor includes a photonic crystal structure and a defect member disposed adjacent the photonic crystal structure. The defect member defines an operative surface. An input light signal from the light source is inputted to the photonic crystal structure and defect member and is internally reflected to thereby output the output signal. Also, the output signal relates to a condition at the operative surface.

Furthermore, a bioassay sensor is disclosed that includes a light source, a sensing device, and a photonic crystal sensor. The photonic crystal sensor includes a photonic crystal structure and a defect member disposed adjacent the photonic crystal structure. The defect member defines an operative surface exposed so as to adsorb material thereon. Input light from the light source is inputted to the photonic crystal structure and defect member and is internally reflected to thereby output an output signal that is detected by the sensing device. The output signal relates to the material adsorbed on the operative surface.

Moreover, an ultrasonic sensor is disclosed that includes a light source, a sensing device, and a photonic crystal sensor. The photonic crystal sensor includes a photonic crystal structure and a defect member disposed adjacent the photonic crystal structure. The defect member defines an operative surface exposed so as to be influenced by an ultrasonic signal. Input light from the light source is inputted to the photonic crystal structure and defect member and is internally reflected to thereby output an output signal that is detected by the sensing device. The output signal relates to the influence of the ultrasonic signal.

In addition, a method of sensing a condition at an exposed operative surface of a photonic crystal sensor is disclosed that includes providing the photonic crystal sensor such that the photonic crystal sensor includes a photonic crystal structure and a defect member disposed adjacent the photonic crystal structure. The defect member defines the exposed operative surface. The method also includes inputting an input light signal from a light source to the photonic crystal structure and defect member such that the input light signal is internally reflected and such that an output signal is outputted from the photonic crystal sensor. Furthermore, the method includes detecting the output signal to thereby detect the condition at the exposed operative surface.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

Figure 1:
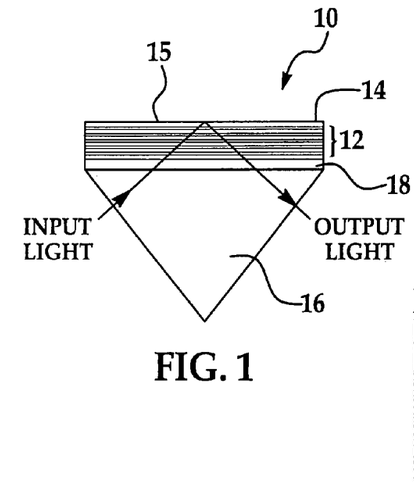
FIG. 1 is cross sectional view of one embodiment of a photonic crystal (PC) sensor constructed according to the present disclosure.

Referring initially to FIG. 1, one embodiment of a photonic crystal (PC) sensor 10 is illustrated. In the embodiment shown, the PC sensor 10 includes a PC structure 12, a defect member 14 disposed adjacent the PC structure 12 on one side, and a prism 16 disposed adjacent the PC structure 12 on an opposite side. The defect member 14 defines an operative surface 15. Also, a substrate 18 is interposed between the PC structure 12 and the prism 16. The input light has total internal reflection (TIR) at the sensor top surface. Owing to the TIR, an imaginary PC structure exists, which results in a unique open microcavity.

As will be discussed in greater detail below, only one PC is used in a total internal reflection (TIR) geometry instead of a prior art closed cavity with two pieces of PCs. Thus, the PC sensor 10 is open and exposed, and can be easily influenced by other molecules or signals to be detected. The reflection spectrum of the PC structure is extremely sensitive to changes in thickness of the defect member 14 and/or to the refractive index of biomolecules bound to the defect member 14. Thus, using the PC sensor 10 in this unique configuration opens up a wide range of applications and forms the basic detection mechanism for constructing highly sensitive sensors for various situations.

As shown, input light from a light source (not shown) is inputted to the prism 16, the input light passes through the prism 16, the substrate 18, the PC structure 12, and the defect member 14 if a resonance condition is satisfied in the defect member 14. Then, the input light is totally internally reflected at the operative surface 15. If a resonance condition is not satisfied in the defect member 14, the input light merely passes through the prism 16 and the substrate 18, while it gets highly reflected by the PC structure. A light signal is outputted from the PC sensor 10. As will be discussed in greater detail below, the output light signal is monitored in order to detect a condition at the operative surface 15. For instance, the PC sensor 10 can be used for biomolecular assay or as an ultrasonic sensor.

The PC structure 12 includes a plurality of alternating pairs of layers of different dielectric materials. In one embodiment, each dielectric material has a different refractive index. In one embodiment, there are seven alternating layers of silica and hafnia with the top layer (i.e., the layer on which the defect member 14 is provided) being hafnia. Also, in this embodiment, the substrate 18 is made of glass. Moreover, the defect member 14 is made of silica and has a thickness that is different than the thickness of any of the layers within the PC structure 12. In another embodiment, the defect member 14 includes a plurality of layers of different materials. In addition, the defect member 14 includes an absorbing material in one embodiment. It will be appreciated that the materials used to make the PC structure 12, the substrate 18, and/or the defect member 14 could be of any suitable type without departing from the scope of the present disclosure.

Furthermore, in one embodiment, the thickness of each dielectric layers in the PC structure 12 is determined according to the following considerations. It is assumed that the incident angle at the substrate layer 18 is $\theta_i$. The refraction angles in the substrate 18, the silica layers of the PC structure 12, the hafnia layers of the PC structure 12, and the defect member 14 are $\theta_s$, $\theta_A$, $\theta_B$, and $\theta_X$, respectively. Also, $n_s$, $n_A$, $n_B$, and $n_X$ are the refractive index of the substrate 18, the silica layers of the PC structure 12, the hafnia layers of the PC structure 12, and the defect member 14, respectively. Therefore:

$$n_s \sin\theta_s = n_A \sin\theta_A, \; n_s \sin\theta_s = n_B \sin\theta_B, \; n_s \sin\theta_s = n_x \sin\theta_x \quad (1)$$

The thickness of the dielectric layers in the PC structure 12 satisfies the following relation:

$$n_A d_A \cos\theta_A = n_B d_B \cos\theta_B = \frac{\lambda}{4} \quad (2)$$

where $\lambda$ is the center wavelength of the photonic band gap, and $d_A$ and $d_B$ are the thickness for the silica layers and hafnia layers, respectively.

From Eqs. (1) and (2), we obtain, $$d_A = \frac{\lambda}{4(n_A^2 - n_S^2 \sin^2 \theta_S)^{1/2}}, \quad d_B = \frac{\lambda}{4(n_B^2 - n_S^2 \sin^2 \theta_S)^{1/2}} \quad (3)$$

In order to obtain local field enhancement in the defect member 14, the thickness of the defect member 14 satisfies the following resonant condition, $$2 n_X d_X \cos\theta_X + \alpha \frac{\lambda_d}{2\pi} = \frac{\lambda_d}{2} \quad (4)$$

where $\alpha$ represents the Goos Hänchen phase shift, and $\lambda_d$ is the wavelength of the photonic defect state, which should be within the photonic band gap. The factor of 2 in the first term on the left hand side of equation 4 is due to the fact that the light double passes the defect member due to the TIR. From Eqs. (1) and (4), we have, $$d_X = \frac{(\pi - \alpha)\lambda_d}{4\pi(n_X^2 - n_S^2 \sin^2 \theta_S)^{1/2}} \quad (5)$$

For s-polarization of incident light, the Goos Hänchen phase shift is given by the following expression:

$$\alpha_s = -2\tan^{-1}\left(\frac{n_t \left(\frac{\sin^2 \theta_X}{\sin^2 \theta_C} - 1\right)^{1/2}}{n_X \cos\theta_X}\right) = -2\tan^{-1}\left(\left(\frac{n_S^2 \sin^2 \theta_S - n_t^2}{n_X^2 - n_S^2 \sin^2 \theta_S}\right)^{1/2}\right) \quad (6)$$

where $n_t$ is the refractive index of the media on the defect member, and $\theta_C$ is the critical angle for the TIR. The thickness of the defect member 14 thus is determined according to:

$$d_X = \frac{\lambda_d}{4\pi(n_X^2 - n_S^2 \sin^2 \theta_S)^{1/2}} \left(\pi + 2\tan^{-1}\left(\left(\frac{n_S^2 \sin^2 \theta_S - n_t^2}{n_X^2 - n_S^2 \sin^2 \theta_S}\right)^{1/2}\right)\right) \quad (7)$$

For p-polarization of incident light, the Goos Hänchen phase shift is given by the following expression:

$$\alpha_p = -2\tan^{-1}\left(\frac{n_X}{n_t} \cdot \frac{\left(\frac{\sin^2 \theta_X}{\sin^2 \theta_C} - 1\right)^{1/2}}{\cos\theta_X}\right) = -2\tan^{-1}\left(\left(\frac{n_X}{n_t}\right)^2 \cdot \left(\frac{n_S^2 \sin^2 \theta_S - n_t^2}{n_X^2 - n_S^2 \sin^2 \theta_S}\right)^{1/2}\right) \quad (8)$$

The thickness of the defect member 14 for the p-polarization thus is determined according to:

$$d_X = \frac{\lambda_d}{4\pi(n_X^2 - n_S^2 \sin^2 \theta_S)^{1/2}} \left(\pi + 2\tan^{-1}\left(\left(\frac{n_X}{n_t}\right)^2 \cdot \left(\frac{n_S^2 \sin^2 \theta_S - n_t^2}{n_X^2 - n_S^2 \sin^2 \theta_S}\right)^{1/2}\right)\right) \quad (9)$$

In order to test fluorescence enhancement of the PC sensor 10, the center wavelength is chosen to be 600 nm. A 100 μL of 1 μM ethanol solution of Nile blue, a known dye molecule, is spin coated on the operative surface 15 of the defect member 14. A reference sample (not shown) is also constructed having a substrate deposited with only one silica layer. The same solution Nile blue solution is spin-coated on the reference sample. The reference sample and the PC sensor 10 are placed on a prism with index-matching fluid and excited by a laser output from an optical parametric amplifier tuned to 600 nm in wavelength. The emitted fluorescence is collected with a 20× objective lens and passes through a sharp-cut long-pass filter. A spectrometer coupled with a photon-counting streak scope is used to observe the wavelength- and time-resolved fluorescence.

Figure 2:
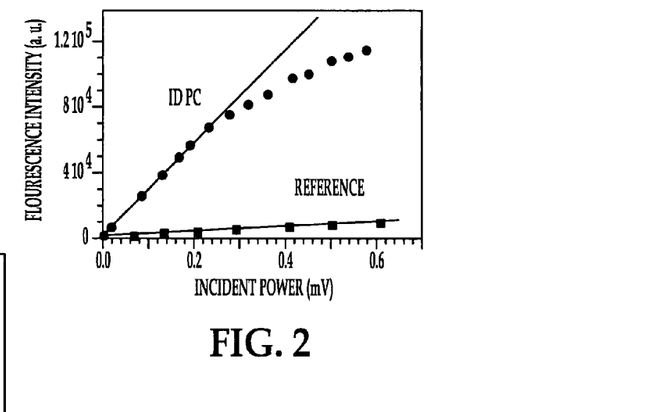
FIG. 2 is a graphical comparison of fluorescence intensity from samples with and without a PC sensor of the type shown in FIG. 1.

The excitation power dependence of the fluorescence intensity is measured. In one embodiment represented in FIG. 2, a saturation of absorption occurs at approximately 0.24 mW excitation power for the PC sensor 10. Before the saturation, the observed fluorescence intensity from the PC sensor 10 was enhanced by 20-fold compared to that from the reference sample without a PC structure.

Figure 3A:
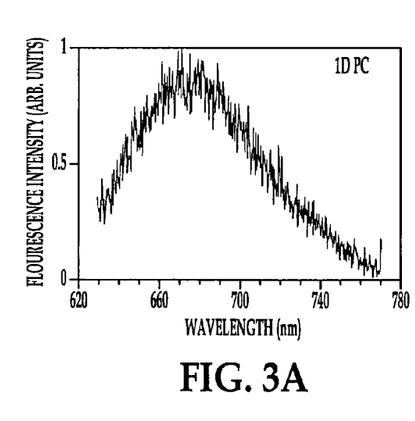
FIG. 3A is a graph of a spectrum curve representing enhanced fluorescence from a PC sensor of the type shown in FIG. 1.
Figure 3B:
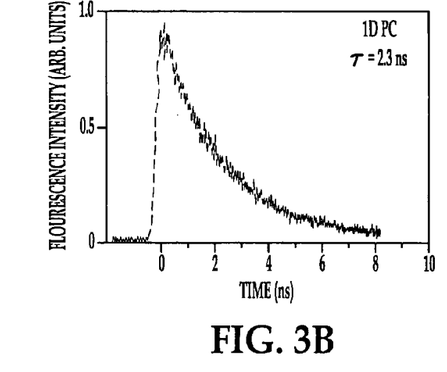
FIG. 3B is a graph of a decay curve representing enhanced fluorescence from a PC sensor of the type shown in FIG. 1.

This result experimentally verifies that a single PC can be used in a TIR geometry to achieve local field enhancement. In addition, the fluorescence spectrum collected from top of the PC-TIR sample is not modified by the photonic band gap structure as represented in FIG. 3A. Also, the fluorescence decay curve shown in FIG. 3B has a decay constant of 2.3 ns, which is in agreement with the value of 2.6 ns for the reference sample within a margin of detection error. These results demonstrate that it is possible to form a microcavity by using only one piece of PC structure in a TIR geometry.

As will be discussed in greater detail below, the operative surface 15 of the defect member 14 is generally exposed so as be affected by external influences to be discussed. As such, the properties of the light reflected at the operative surface 15 will vary depending on the external influences at the operative surface 15. Thus, the output signal from the PC sensor 10 can be monitored for changes in order to detect the condition at the operative surface 15. Accordingly, the PC sensor 10 can be used for various sensing applications, such as kinetic analysis of biomolecular interactions or sensitive ultrasonic detections, and the like.

APPLICATION EXAMPLE 1

Biomolecular Assay

Specific interactions of biological molecules with various ligands, biopolymers, and membranes, such as protein:protein, protein:lipid, protein:DNA and protein:membrane binding, provide a chemical foundation for all cellular processes. The study of these biomolecular affinity and binding kinetics is of great importance for biomedical researches. For example, in order to discover a novel therapeutic antibody to treat cancer and other diseases, screening of a large repertoire of small molecules is necessary in order to identify high specificity and high affinity binders, followed by a more detailed characterization of the binding properties and determination of epitope specificity. Thus, there is an increasing demand for sensitive, accurate and high throughput analytical instruments that can provide insights on a molecular basis into critical biological processes.

One of the most widely used analytical techniques is based on surface plasmon resonance (SPR). In this known technique, a thin noble metal film is placed in an evanescent optical field, and the change of the SPR reports the binding of analytes to the ligand immobilized on the metal surface. Although this method allows label-free, real-time analysis, it has many drawbacks. For example, it is difficult to obtain accurate kinetic analysis due to the mass-transport limitation and it is not suitable for the measurement of small analytes (e.g., ~1000 Da).

However, the PC sensor 10 of the present disclosure has a detection mechanism fundamentally different from the SPR and leads to a significant improvement in detection sensitivity. More specifically, the photonic defect state of the PC sensor 10 is extremely sensitive to the change in the thickness and/or refractive index of the defect member 14, and this characteristic is employed for a sensitive biomolecule analysis tool as described below.

In order to test this tool a PC sensor 10 is constructed that includes a PC structure 12 having three alternating layers of silica and titania disposed on a substrate 18, which is made of BK7 glass. The resonant wavelength is chosen to be 600 nm. The silica and titania layers of the PC structure 12 have a refractive index of 1.458 and 2.225, respectively, and the substrate 18 has a refractive index of 1.516. A defect member 14 with a refractive index of 1.49 is deposited on the top layer (titania) of the PC structure 12. The incident angle in the substrate 18 is chosen to be 68°. For s-polarization input light, the thickness of the silica, titania and the defect member 14 are 388.32 nm, 86.98 nm, and 446.32 nm, respectively, based on Eqs. (3) and (7), assuming the refractive index of the solution in contact with the defect member is 1.333. When the incident light wavelength falls in the photonic band gap, it is reflected by the PC structure 12 and does not reach the defect member 14. When the incident light wavelength matches the photonic defect state, the light reaches the defect member 14 and experiences TIR at the operative surface 15.

Figure 4A:
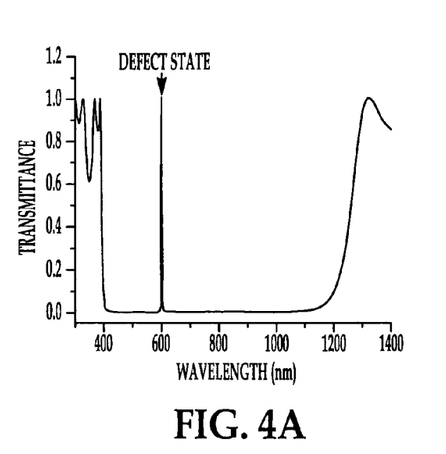
FIG. 4A is a graph of a calculated light spectrum that passes through a PC sensor of the type shown in FIG. 1 without doping of an absorbing material.
Figure 4B:
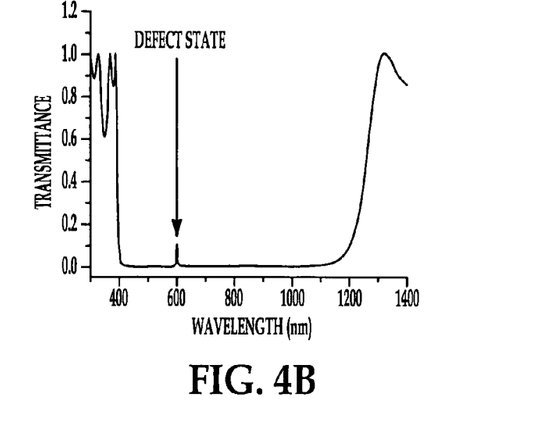
FIG. 4B is a graph of a calculated light spectrum that passes through a PC sensor of the type shown in FIG. 1 doped with absorbing material.

FIG. 4A shows the spectrum of light that reaches the defect member and experiences TIR when there is no absorption in the defect member. When the defect member 14 is doped with some absorbing material, the light is partially absorbed. In the calculation, we assume the extinction coefficient to be 0.0005 in the absorptive defect member 14, which corresponds to about only 0.32% absorption when there is no PC structure 12. FIG. 4B shows the corresponding spectrum in contrast to the case with an absence of absorption. The result shows that the absorption is more than 90%, enhanced by the PC structure 12 comparing 0.32% in the absence of a PC structure 12.

In practice, the portion of light reflected by the PC structure 12 and the portion reflected at the operative surface 15 are mixed and difficult to separate. Therefore, the total amount of the reflected light is used as a measurable quantity.

The defect member 14 is doped with absorbing materials, so that the reflected light that passes through the defect member has lower reflectance, thus resulting a reflectance dip at a specific wavelength corresponding to the defect state within the photonic band gap. When a thin layer is formed on the operative surface 15 (defined as an "adlayer" on the operative surface 15), the wavelength of the reflectance dip varies. It is appreciated that the adlayer could be formed by biological molecules to be observed in a biomolecular assay.

Then, the change in the output signal (i.e,. the reflected light) from the PC sensor 10 is observed in order to detect the condition at the operative surface 15 due to the adlayer. More specifically, in one embodiment, a change in wavelength of the output light signal is detected as shown in FIG. 5 and/or a change in output signal light intensity at a wavelength of 632.8 nm is detected as shown in FIG. 6.

Figure 5:
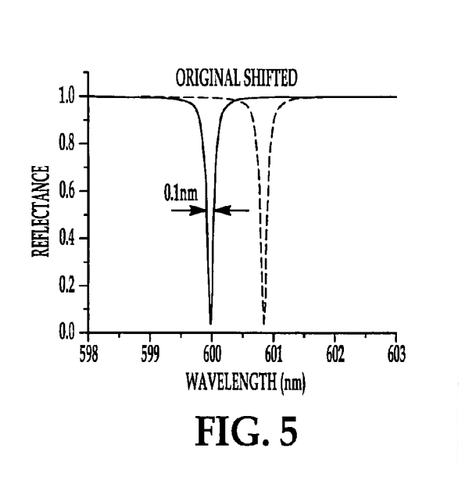
FIG. 5 is a graph showing reflectance spectrum shift for PC sensors of the type shown in FIG. 1 when an adlayer is attached to the operative surface.
Figure 6:
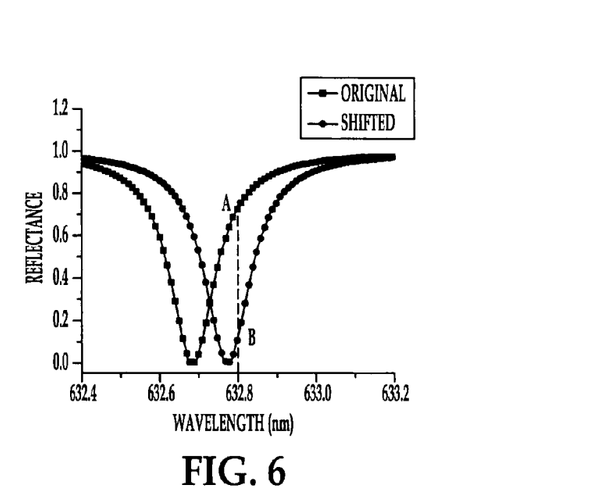
FIG. 6 is a graph showing that the intensity of a reflected light at a fixed wavelength changes if the reflectance spectrum shifts for PC sensors of the type shown in FIG. 1.

Specifically, a sharp and prominent dip appears in the reflection spectrum corresponding to the photonic defect state as shown in FIG. 5. This dip is relatively narrow and the resonant wavelength of this dip is sensitive to the material bound to the operative surface 15. For example, in the embodiment shown in FIG. 5, the dip width is only 0.1 nm and the resonant wavelength is shifted as much as 0.86 nm when the adlayer is 1 nm thick and with a refractive index of 1.46. This spectrum shift can be easily measured since the dip width is extremely narrow. Also, an even narrower dip width, and thus more sensitive detection, can be observed by increasing the incident angle and/or the number of alternating layers of the PC structure. It is noted that although the defect member 14 is absorptive, both immobilized reactants on the operative surface 15 and mobile reactants that form the adlayer need not be labeled. Thus, it is possible to obtain a label-free measurement for the sample of interest.

In addition to directly measuring the spectrum shift with a spectrometer, a differential reflectance measurement is employed at a fixed wavelength. FIG. 6 shows that the reflectance changes as much as 85.24% at the wavelength of a HeNe laser (632.8 nm), when a 0.1-nm thin adlayer with refractive index of 1.46 is formed on the sensor surface. Since a detection accuracy of $10^{-4} \sim 10^{-5}$ can be obtained in a typical differential reflectance measurement, an extremely high detection sensitivity of molecular binding on the sensor surface can be achieved. The detectable adlayer thickness can be as small as $10^{-5} \sim 10^{-6}$ nm. This is a significant improvement compared with the sensitivity of an SPR based instrument.

Besides higher detection sensitivity, the detection system using the PC sensor 10 has many other advantages over the SPR based detection, such as larger detection range, better baseline stability and flexible detection configurations. These advantages are described below.

Using the PC sensor 10, the adlayer is in the actual optical path of the input light signal, which increases the optical path length of the defect member 14. The reflectance dip of the photonic defect state shifts within the photonic bandgap of the PC structure 12 when the adlayer thickness and/or refractive index changes. The detection range is therefore restricted by the bandgap, which is around 700 nm for the PC structure 12 with three pairs of alternating dielectric layers and an incident angle of 68°. The detection range can be even wider by increasing the incident angle. In contrast, the detection range of an SPR instrument is limited to the range of the evanescent field, which is typically around 200 nm. Thus, the PC sensor 10 can be used to detect thicker adlayers or bigger particles compared to SPR measurements.

Figure 7:
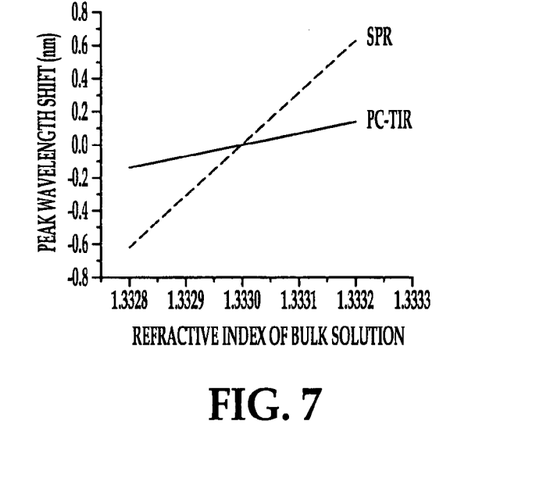
FIG. 7 is a graph showing a baseline shift comparison between SPR detection and PC detection.

Also, for the detection range on the small side, a critical factor is the detection baseline stability. A small change in refractive index of the solution on the sensor surface may cause a resonant wavelength variation. There may be several causes for changes in the refractive index, such as the temperature. The evanescent field in SPR has a large portion (relative to the thin adlayer) in the bulk solution. The change in the refractive index of the solution contributes to the shift of SPR wavelength in the same way as the adlayer. A small change in the solution property results in nonnegligible fluctuation in the detection baseline. For example, when the refractive index of solution changes only by 0.0002, the SPR baseline drift is as large as 0.62 nm, which is equivalent to the change when a 0.25-nm adlayer with refractive index of 1.46 is attached to the defect member 14. On the other hand, the adlayer interacts with a propagating field in the PC sensor 10 and increases the actual optical path, while the contribution to the change in resonant wavelength from the solution is due to the Goos Hänchen phase shift, which is very small. Thus, the resonant wavelength is less affected by the solution. For the same change in the solution, the resonant wavelength of the PC sensor 10 shifts just 0.14 nm. FIG. 7 shows the comparison of baseline shift caused by very small fluctuations in the refractive index of bulk solution between SPR and PC-TIR detection.

In the SPR based measurements, the refractive index and thickness of the adlayer cannot be independently determined; one has to use the value of one of the parameters given by other measurements in order to calculate the value of the other parameter. In contrast, the refractive index and thickness of the adlayer can be independently determined using the PC sensor 10. The resonant wavelength shift of the defect state varies with the angle or polarization of the incident light, and this dependence is different for different refractive index of the adlayer. Thus, one obtains both the refractive index and adlayer thickness by carrying out the measurement with two different incident angles or two different polarizations.

Figure 8:
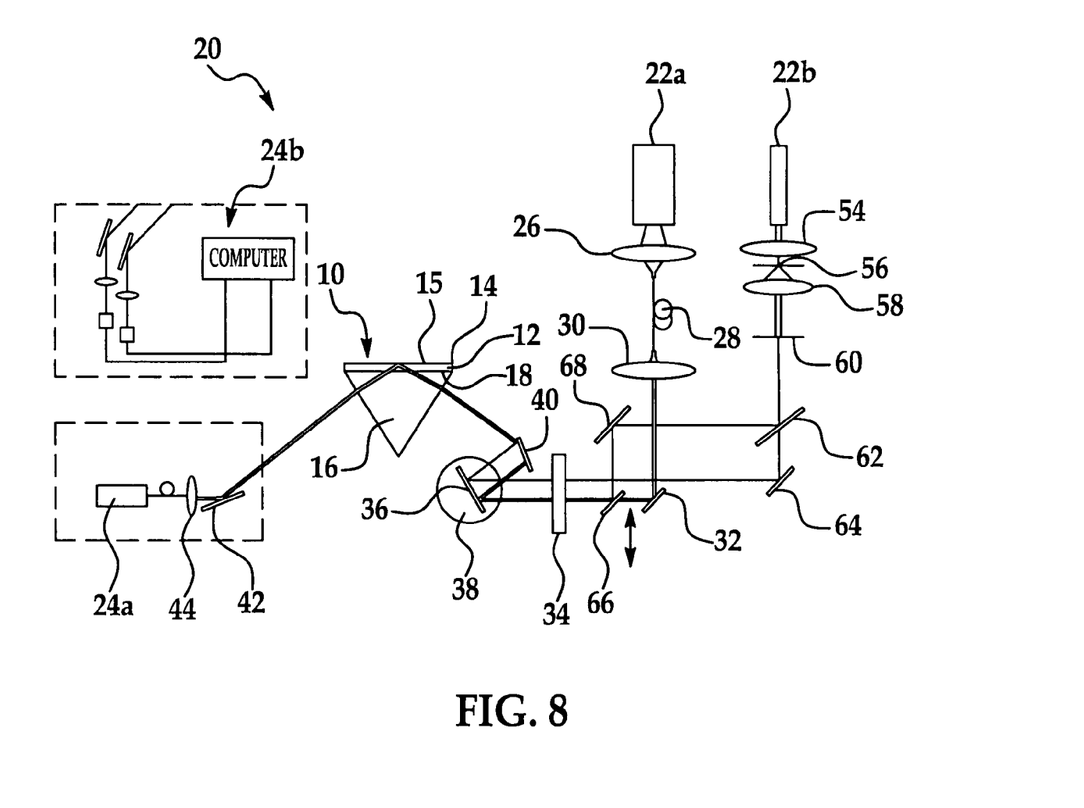
FIG. 8 is a schematic diagram of a detection system employing a PC sensor of the type shown in FIG. 1.

Referring now to FIG. 8, one embodiment of a detection system 20 employing a PC sensor 10 is shown. In this embodiment, the detection system 20 is a bioassay system. The detection system 20 is modular because it includes a plurality of light sources 22a, 22b and a plurality of sensing devices 24a, 24b. In the embodiment shown, the detection system 20 can be used to detect spectral shift of the output signal and/or differential reflectance of the output signal.

Using the white light source 22a, the reflectance spectrum is obtained using the PC sensor 10. A large detection range (about 1~700 nm) of adlayer thickness can be obtained. When the differential reflectance measurement is used, extremely high detection sensitivity can be achieved and the detectable range of the adlayer thickness is from 1 nm down to $10^{-5}$ nm.

In order to detect spectral shift, light from a broad band white light source 22a is directed through a first lens 26 and is coupled into a single-mode (SM) fiber 28 to get a good optical mode, and the output beam from the fiber 28 is collimated with a second lens 30. The light from the white light source 22a is then reflected by a first reflecting mirror 32 and through a linear polarizer 34 to adjust the light polarization. The light is reflected by a second reflecting mirror 36 that is mounted on a rotator 38. The position of the rotator 38 is controlled by a computer to adjust the incident angle. The light is then reflected again by a third reflecting mirror 40. The light enters the PC sensor 10 through the prism 16, is totally internally reflected at the operative surface 15 for the wavelength component that satisfies the resonance condition, or is reflected by the PC structure 12 for the other wavelength components. The total output signal from the PC sensor 10 is reflected by a fourth reflecting mirror 42, passes through a third lens 44, and is directed into a spectrometer sensing device 24a. Thus, the spectral shift of the output signal can be detected.

To detect differential reflectance with the detection system 20, a laser 22b is used as the light source. In one embodiment, the laser 22b is a HeNe laser 22b with the wavelength of 632.8 nm. Also, the PC sensor 10 includes a two-part structure represented in FIG. 9. On a first portion 50 of the operative surface 15, molecular binding occurs and an adlayer 51 is formed thereon. A second portion 52 of the operative surface 15 remains unchanged. As shown in FIG. 8, the laser beam passes through a fourth lens 54, through a pinhole 56, through a fifth lens 58, and through a diaphragm 60. Then, the laser beam is split into two by a splitter 62. One of the split beams is reflected by a fifth reflecting mirror 64, through the polarizer 34, and is reflected by the second and third reflecting mirrors 36, 40 to thereby illuminate the first portion 50 of the operative surface 15 having the adlayer 51. The other of the split beams is reflected by a sixth and seventh reflecting mirror 68, 66, through the polarizer 34, and is reflected by the second and third reflecting mirrors 36, 40 to thereby be directed at the second portion 52 of the operative surface 15 as a reference. The intensities of the two reflected beams are monitored by a second sensing device 24b having two identical detectors. The intensity ratio between the two beams is recorded, which sensitively reflects the property of the adlayer 51.

Figures 9, 10, 11A, 11B:
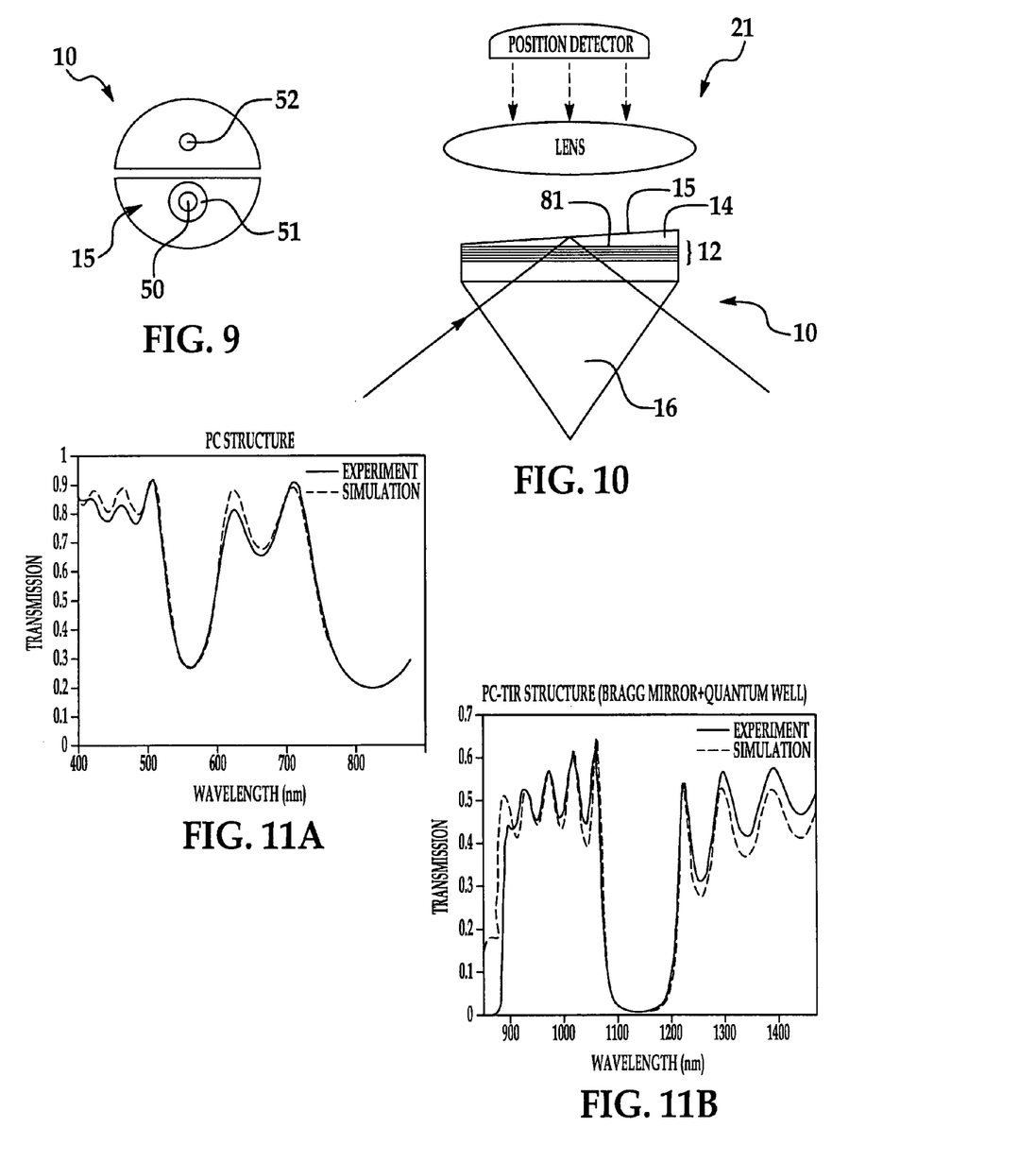
FIG. 9 is a top view of a PC sensor for differential reflectance measurements.
FIG. 10 is a side view of another embodiment of a detection system employing a PC sensor with a defect member having an angled shape.
FIG. 11A is a graph showing experimental and calculated transmission spectra at normal incident direction for a PC sensor fabricated by an electron-beam evaporation method.
FIG. 11B is a graph showing experimental and calculated transmission spectra at normal incident direction for a PC sensor fabricated by a MBE method.

Referring now to FIG. 10, another embodiment of a detection system 21 is illustrated. In this embodiment, the PC sensor 10 includes a defect member 14 having an operative surface 15 that is angled. More specifically, the operative surface 15 is angled so as to define a plane that intersects a plane defined by an opposite side 81 of the defect member 14.

The position where TIR occurs is observed. As shown, for a fixed incident angle and certain wavelength of incident light, the TIR occurs at a position where the defect member 14 thickness satisfies the resonance condition. Thus, by monitoring the position of TIR one can use the PC sensor 10 to detect if there is something (e.g. biomolecules) bound to the defect member 14 or if there is some signal that changes the thickness of the defect member 14.

Two techniques can be used to fabricate the PC sensor 10 for use in the detection system 20 shown in FIG. 8. First, electron-beam evaporation can be used. Silica, Titania and pure silicon are used as the target materials. Rutherford backscattering spectroscopy (RBS) is used to calibrate the thickness of deposited layers. The transmission spectrum of PC structure 12 and defect member 14 composed of silicon and silica at normal incident direction is measured, which is in agreement with simulation results as shown in FIG. 11A. Second, fifteen pairs of GaAs/AlAs layers are grown on a GaAs substrate 18 by MBE with high accuracy (~0.1 nm). InxGa1-xAs (x=0.4) is used as the absorptive layer and its thickness (d=8 nm) is decided by considering both resonant dip depth and growing mismatch with GaAs. Another GaAs layer is added on top of InxGa1-x As to satisfy the resonant condition in the defect member. FIG. 11B shows the measured and calculated transmission spectrum at normal incident direction. The good agreement between the theoretical calculation and experimental result indicate that the PC sensor 10 is well fabricated.

In one embodiment, the PC sensor 10 is made by electron-beam evaporation. The thickness of the three pairs of Silica and Titania alternating layers in the PC structure 12 is 438 nm and 87 nm, respectively. Its defect member 14 is composed of 18-nm Silicon and 140-nm Silica.

Figure 12A:
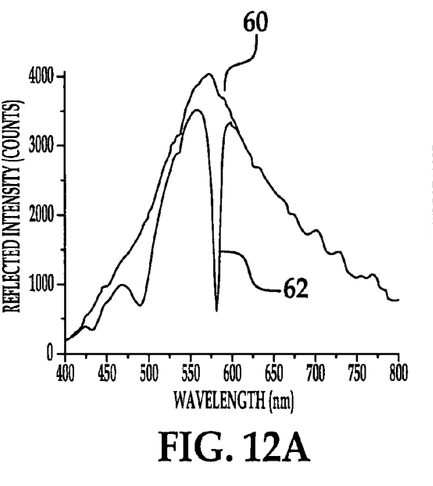
FIG. 12A is a graph showing a spectrum of a light source and a reflected light spectrum for a PC sensor.
Figure 12B:
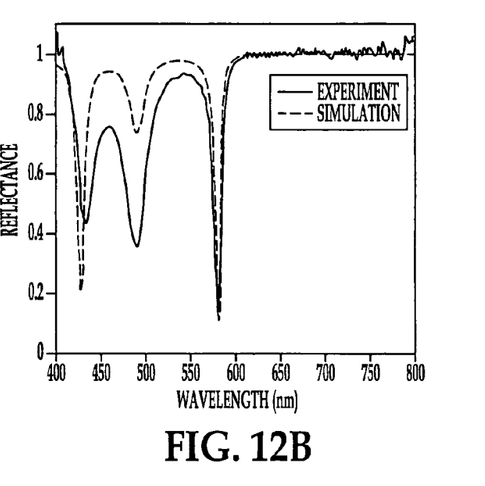
FIG. 12B is a graph showing an experimental and simulated PC reflectance spectrum.

FIG. 12A shows the light intensity of a broad band white light source reflected from the PC sensor 10 (as indicated by the curve 60) and a reference substrate (as indicated by the curve 62) used in a total internal geometry. FIG. 12B shows the experimental and simulated PC-TIR reflectance spectrum. In the calculation, the thickness of different layers are taken from the measured values, and the refractive indices of the substrate 18 (e.g., BK7), Silica and titania are 1.516, 1.458 and 2.225, respectively, at the wavelength of 600 nm. The refractive index and extinction coefficient of silicon are 3.94 and 0.0183 at 600 nm, respectively. The solvent used on the operative surface 15 is de-ionized (DI) water with a refractive index of 1.333. The incident angle is 64.5°. Both the simulation and experimental results show a primary resonance dip at 580 nm with a narrow width of 8 nm. The dip width is much narrower than that of a typical SPR resonance spectrum width (40 nm).

Figure 13A:
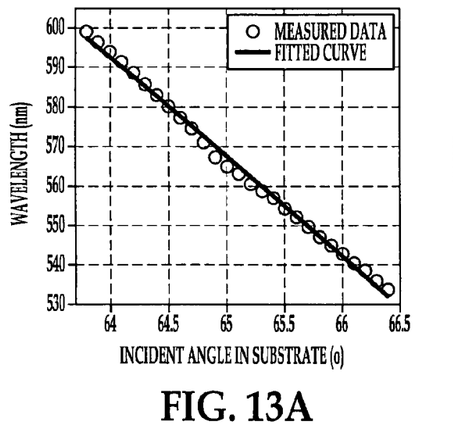
FIG. 13A is a graph showing a relationship between resonant wavelength and incident angle for a PC sensor.
Figure 13B:
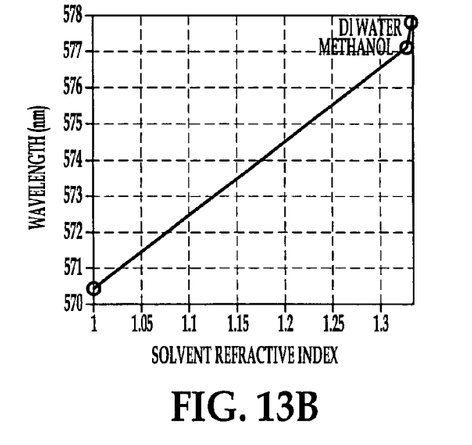
FIG. 13B is a graph showing a relationship between resonant wavelength and solvent refractive index for a PC sensor.
Figure 13C:
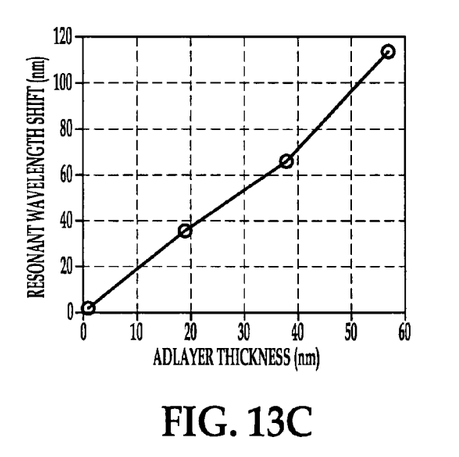
FIG. 13C is a graph showing a relationship between resonant wavelength shift and adlayer thickness for a PC sensor.

Accordingly, the resonant wavelength shifts to longer wavelength with decreasing the incident angle as shown in FIG. 13A. In addition, the dependence of the resonance wavelength on solvents is measured as shown in FIG. 13B. The resonant wavelength shift is only 150 nm per RIU for the solvent with a refractive index close to water. This small shift is preferred in order to have a system with high stability because a small temperature fluctuation may cause the change in solvent refractive index. The refractive index of water is known to decrease by ~$8\times10^{-5}$ RIU per degree K near room temperature. Using the solvent refractive index dependence of the resonance wavelength shift 150 nm/RIU, the temperature stability of the PC-TIR system is −0.012 nm/K, which is remarkably improved comparing with that of an SPR system (i.e., −0.25 nm/K). The dependence of the resonant wavelength shift on the adlayer properties is also shown in FIG. 13C. As shown, the resonant wavelength sensitively shifts to longer wavelength with increasing the adlayer thickness.

Figure 14:
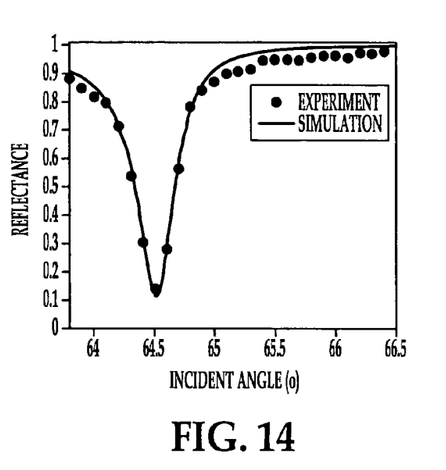
FIG. 14 is a graph showing incident angle dependence of the reflectance for a PC sensor at a fixed wavelength.

In addition, the resonance dip is measured as a function of the incident angle for a fixed wavelength of 580 nm as shown in FIG. 14. The full width at half maximum is only 0.4°, which is about five times smaller than that in an SPR system. The experimental result is again in a good agreement with a simulation.

The PC sensor 10 also has an extremely high sensitivity in the differential reflectance measurement. Detection of a thin monolayer of small molecules can be carried out. For instance, the PC sensor 10 is first exposed to 5% APTES solutions for 20 minutes, then rinsed with de-ionized (DI) water and methanol and dried with nitrogen. After the silanization, the PC sensor 10 is exposed to a 2.5% glutaraldehyde solution in 20 mM HEPES buffer (pH=7.4) for 30 minutes, then rinsed with DI water and dried with nitrogen. A thin layer of Glutaraldehyde molecules are obtained due to its reaction with the amino groups on the silanized surface. The total thickness of the APTES/glutaraldehyde layer is 1.5 nm.

Figure 15:
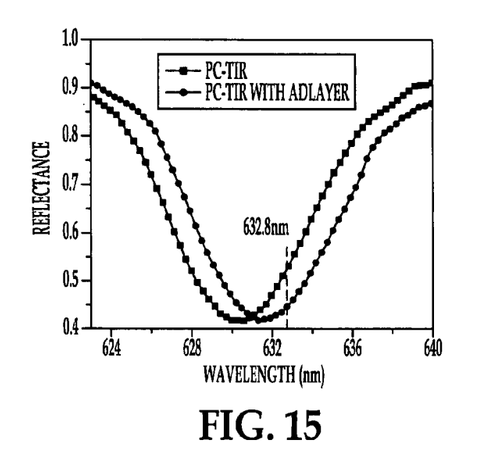
FIG. 15 is a graph showing reflectance spectra of a PC sensor with and without an adlayer.

A resonance dip shift by 1.24 nm is observed in the reflectance spectrum measurement as shown in FIG. 15, when the APTES/glutaraldehyde adlayer is formed. In order to achieve higher sensitivity, differential reflectance measurements with a HeNe laser are used.

Figure 16A:
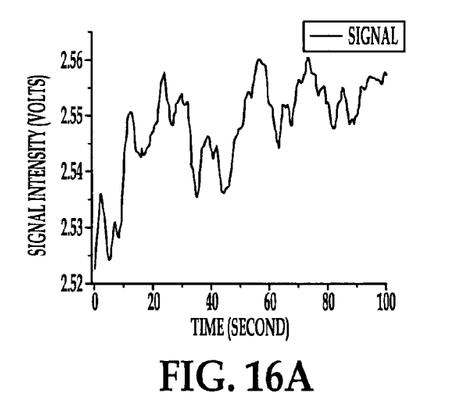
FIG. 16A is a graph showing a signal intensity for a PC sensor.
Figure 16B:
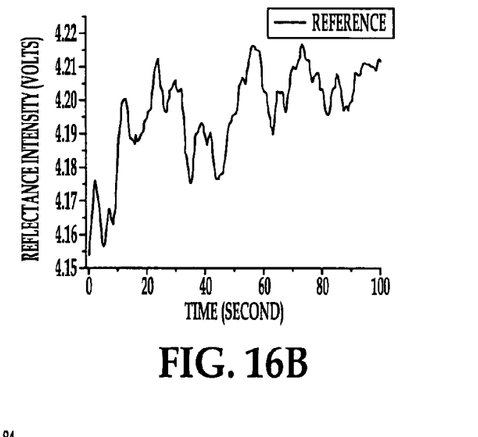
FIG. 16B is a graph showing a reference intensity for a PC sensor.
Figure 16C:
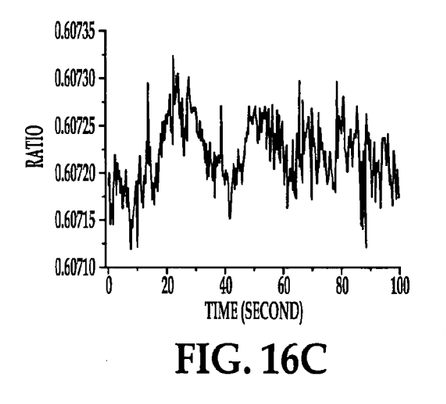
FIG. 16C is a graph showing a ratio between the signal and reference channels for a PC sensor.

The intensity stability of the HeNe laser is measured to be about 2% as shown in FIGS. 16A and 16B. A clear improvement of the detection accuracy is obtained by measuring the intensity ratio between these two beams. The fluctuation of the ratio is less than $1.6\times10^{-4}$ as shown in FIG. 16C.

Figure 17:
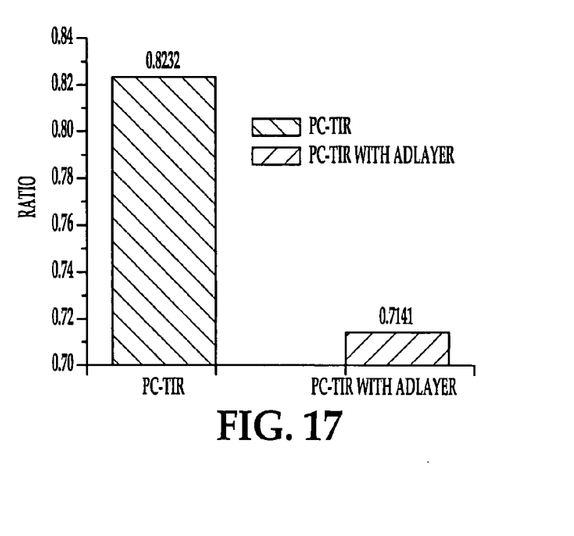
FIG. 17 is a graph showing an intensity ratio change of a PC sensor.

Furthermore, a clear ratio change from 0.8232 to 0.7141 is observed (FIG. 17) when the thin APTES/glutaraldehyde adlayer is formed on the PC sensor 10.

The detection sensitivity of the sensor is expressed as, $$\text{Sensitivity} = \text{Adlayer Thickness} \times \frac{\text{Detection Accuracy}}{\text{Ratio Change}}$$

Since the system has detection accuracy up to $1.6\times10^{-4}$, and the ratio change is 0.1091 for a 1.5 nm adlayer, the detection sensitivity of the PC sensor 10 is 0.002 nm, which is significantly improved compared with the sensitivity of an SPR based instrument.

Figure 18:
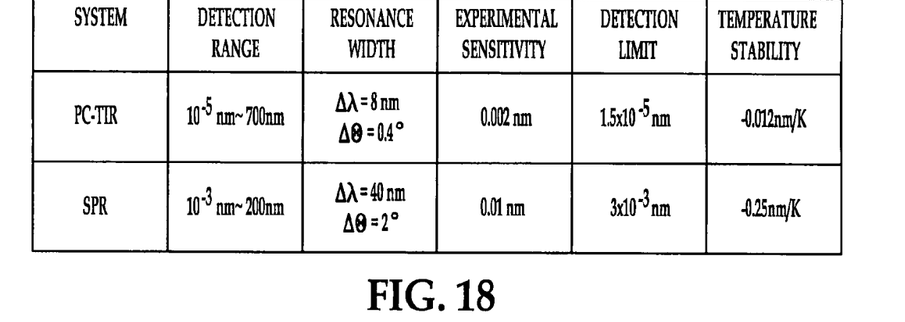
FIG. 18 is a table showing a comparison between PC and SPR systems.

The theoretical detection limit is calculated using our simulation results. For a PC sensor 10 with three alternating layers in the PC structure 12, the resonance dip width is calculated to be 2 nm. A detection limit of $1.5\times10^{-5}$ nm can be predicted for a PC sensor 10, which is in contrast to $3\times10^{-3}$ nm for an SPR system. A comparison between the PC sensor 10 and SPR systems is shown in FIG. 18.

Thus, the PC sensor 10 offers the ability to perform real-time and label-free quantitative detections, allowing for a wide range of biomolecular assays with a higher sensitivity and better stability compared to known SPR-based instruments. In addition, the PC sensor 10 can independently determine the refractive index and thickness of the adlayer.

APPLICATION EXAMPLE 2

Ultrasonic Detector

Figures 19A, 19B:
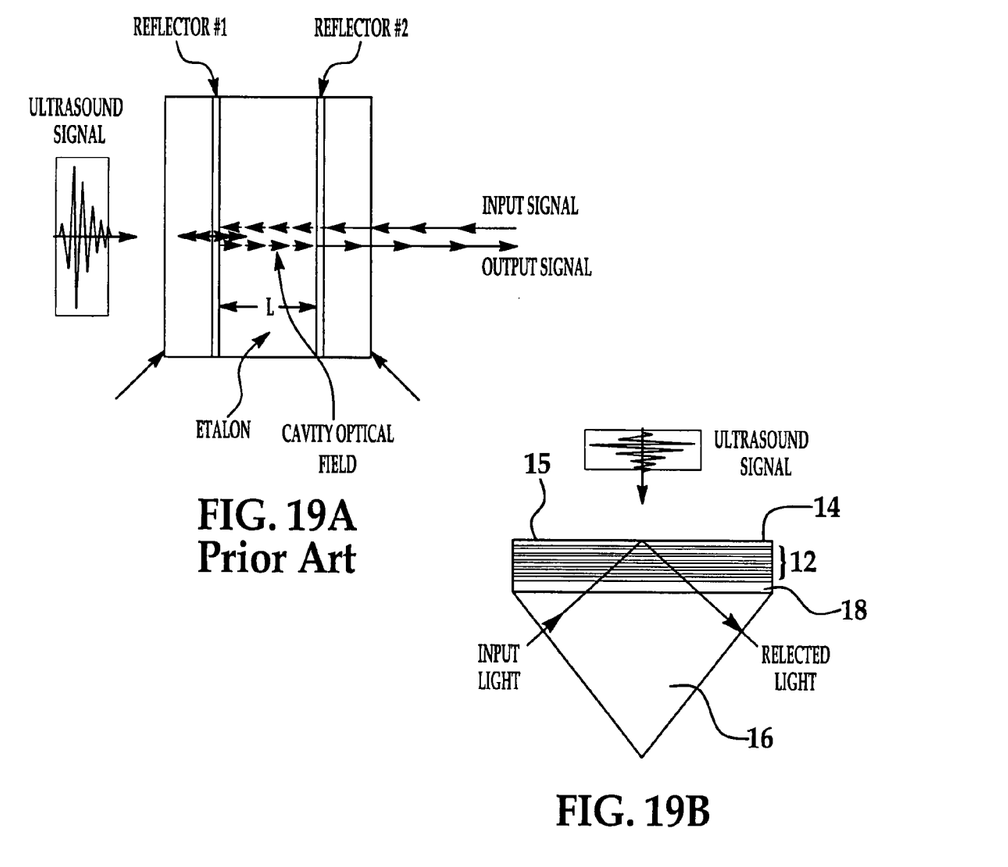
FIG. 19A is a cross sectional view of a prior art etalon ultrasound sensor.
FIG. 19B is a cross sectional view of a PC ultrasound sensor.

The PC sensor 10 can also be employed in an ultrasonic detector. Specifically, the exposed operative surface 15 enables use of the PC sensor 10 as an ultrasonic detector. Optical detection of ultrasound by using an etalon has been demonstrated as shown in FIG. 19A. As shown, the incident and reflected optical signals are presented as spatially separate but, in practice, are collinear. Acoustic displacement at the etalon surface changes the cavity length, which in turn changes the intensity of the optical signal reflected from the etalon. However, the closed structure of the etalon limits the detection sensitivity.

On the other hand, by using the PC sensor 10, the etalon cavity is opened so that the sensor interface can directly interact with the ultrasonic signals. As such, a material with large elasticity can be used as the defect member 14, which is difficult to use in a closed etalon cavity because the two high reflection surfaces are intended to remain parallel to each other and flat. Thus, larger change of the optical response to an ultrasonic signal can be obtained compared with prior art detection using an etalon. In addition, the PC sensor 10 has advantages in optical generation of ultrasound. Because the optical field is enhanced at the operative surface 15 of the defect member 14 of the PC sensor 10, the ultrasonic signal is generated and propagates directly from the operative surface 15 without attenuation by any other additional layers, thus allowing strong ultrasound generations. The PC sensor 10 therefore makes it possible to integrate a strong optical ultrasound generator with a sensitive optoacoustic receiver.

The invention has been described in an illustrative manner. It is to be understood that the terminology which has been used is intended to be in the nature of words of description rather than of limitation. Many modifications and variations are possible in light of the above teachings. Therefore, within the scope of the appended claims, the invention may be practiced other than as specifically described.

What is claimed is:

1. A photonic crystal sensor for outputting an output signal using a light source comprising:
   a photonic crystal structure; and
   a defect member disposed adjacent the photonic crystal structure, the defect member defining an operative surface,
   wherein an input light signal from the light source is inputted to the photonic crystal structure and defect member and is internally reflected to thereby output the output signal,
   wherein the output signal relates to a condition at the operative surface.

2. The photonic crystal sensor of claim 1, wherein the condition at the operative surface is detected by detecting a change in the output signal.

3. The photonic crystal sensor of claim 2, wherein the change in the output signal is at least one of a change in spectrum of the output signal and a change in intensity of the output signal.

4. The photonic crystal sensor of claim 1, wherein the condition at the operative surface is detected by detecting the resonant angle of the input light.

5. The photonic crystal sensor of claim 1, wherein a parameter that affects the condition at the operative surface is determined by measuring the output signal at least one of:
   a plurality of input light angles; and
   polarizations of the input light.

6. The photonic crystal sensor of claim 1, further comprising a prism disposed adjacent the photonic crystal structure, wherein the input light signal from the light source is inputted to the prism.

7. The photonic crystal sensor of claim 6, further comprising a substrate interposed between the prism and the photonic crystal structure.

8. The photonic crystal sensor of claim 1, wherein the photonic crystal structure includes a plurality of alternating pairs of layers of dielectric material, and wherein each dielectric material has a different refractive index.

9. The photonic crystal sensor of claim 8, wherein the plurality of alternating pairs of layers of dielectric material comprises at least one of silica, titania, hafnia, GaAs, and AlAs.

10. The photonic crystal sensor of claim 1, wherein the defect member contains an absorbing material.

11. The photonic crystal sensor of claim 1, wherein the defect member includes a plurality of layers of different material.

12. The photonic crystal sensor of claim 1, wherein the thickness of the defect member, $d_x$, is determined by the resonant condition in the defect member.

13. The photonic crystal sensor of claim 12, further comprising a substrate on which the photonic crystal structure is disposed, and wherein for s-polarization input light, a thickness of the defect member, $d_x$, is defined according to:

$$d_X = \frac{\lambda_d}{4\pi(n_X^2 - n_S^2\sin^2\theta_S)^{1/2}}\left(\pi + 2\tan^{-1}\left(\left(\frac{n_S^2\sin^2\theta_S - n_t^2}{n_X^2 - n_S^2\sin^2\theta_S}\right)^{1/2}\right)\right)$$

wherein $\lambda_d$ is a wavelength of a photonic defect state, $n_x$ is a refractive index of the defect member, $n_s$ is a refractive index of the substrate, $\theta_s$ is a refraction angle in the substrate, and $n_t$ is a refractive index of media on the defect member.

14. The photonic crystal sensor of claim 12, further comprising a substrate on which the photonic crystal structure is disposed, and wherein for p-polarization input light, a thickness of the defect member, $d_x$, is defined according to:

$$d_X = \frac{\lambda_d}{4\pi(n_X^2 - n_S^2\sin^2\theta_S)^{1/2}}\left(\pi + 2\tan^{-1}\left(\left(\frac{n_X}{n_t}\right)^2 \cdot \left(\frac{n_S^2\sin^2\theta_S - n_t^2}{n_X^2 - n_S^2\sin^2\theta_S}\right)^{1/2}\right)\right)$$

wherein $\lambda_d$ is a wavelength of a photonic defect state, $n_x$ is a refractive index of the defect member, $n_s$ is a refractive index of the substrate, $\theta_s$ is a refraction angle in the substrate, and $n_t$ is a refractive index of media on the defect member.

15. The photonic crystal sensor of claim 1, further comprising a substrate on which the photonic crystal structure is disposed, and wherein a layer thickness of a first dielectric material in the photonic crystal structure, $d_A$ is defined according to:

$$d_A = \frac{\lambda_d}{4(n_A^2 - n_S^2\sin^2\theta_S)^{1/2}}$$

wherein $\lambda$ is a center wavelength of a photonic band gap, $n_A$ is a refractive index of the first dielectric material, $n_s$ is a refractive index of the substrate, and $\theta_s$ is a refraction angle in the substrate.

16. The photonic crystal sensor of claim 1, wherein the operative surface is on a side of the defect member opposite to that of the photonic crystal structure so as to be exposed to external effects that alter the condition at the operative surface.

17. The photonic crystal sensor of claim 16, wherein the external effects are at least one of material adsorbed on the operative surface and ultrasonic input.

18. The photonic crystal sensor of claim 1, wherein the operative surface is angled so as to define a plane that intersects a plane defined by an opposite side of the defect member.

19. The photonic crystal sensor of claim 18, wherein the change on the operative surface is detected by measuring the location of total internal reflection at the defect member.

20. A bioassay sensor comprising
   a light source;
   a sensing device;
   and a photonic crystal sensor comprising:
      a photonic crystal structure; and
      a defect member disposed adjacent the photonic crystal structure, the defect member defining an operative surface exposed so as to adsorb material thereon,
   wherein input light from the light source is inputted to the photonic crystal structure and defect member and is internally reflected to thereby output an output signal that is detected by the sensing device, wherein the output signal relates to the material adsorbed on the operative surface.

21. An ultrasonic sensor comprising:
   a light source;
   a sensing device;
   and a photonic crystal sensor comprising:
      a photonic crystal structure; and
      a defect member disposed adjacent the photonic crystal structure, the defect member defining an operative surface exposed so as to be influenced by an ultrasonic signal,
   wherein input light from the light source is inputted to the photonic crystal structure and defect member and is internally reflected to thereby output an output signal that is detected by the sensing device, wherein the output signal relates to the influence of the ultrasonic signal.

22. A method of sensing a condition at an exposed operative surface of a photonic crystal sensor comprising:
   providing the photonic crystal sensor such that the photonic crystal sensor comprises a photonic crystal structure and a defect member disposed adjacent the photonic crystal structure, wherein the defect member defines the exposed operative surface;
   inputting an input light signal from a light source to the photonic crystal structure and defect member such that the input light signal is internally reflected and such that an output signal is outputted from the photonic crystal sensor; and
   detecting the output signal to thereby detect the condition at the exposed operative surface.

* * * * *